US008017910B2

(12) United States Patent
Sharpe (10) Patent No.: US 8,017,910 B2
(45) Date of Patent: Sep. 13, 2011

(54) METHOD FOR PREDICTING HYDROCARBON PROCESS STREAM STABILITY USING NEAR INFRARED SPECTRA

(75) Inventor: Ron Sharpe, Hampshire (GB)

(73) Assignee: Nalco Company, Naperville, IL (US)

( * ) Notice: Subject to any disclaimer, the term of this patent is extended or adjusted under 35 U.S.C. 154(b) by 389 days.

(21) Appl. No.: 12/254,519

(22) Filed: Oct. 20, 2008

(65) Prior Publication Data
US 2010/0096552 A1  Apr. 22, 2010

(51) Int. Cl.
*G01J 5/02* (2006.01)
(52) U.S. Cl. ............... 250/339.01; 250/253; 250/255; 250/338.1; 250/339.07; 250/339.12
(58) Field of Classification Search .............. 250/253, 250/255, 338.1, 339.01, 339.07, 339.12
See application file for complete search history.

(56) References Cited

U.S. PATENT DOCUMENTS

| | | | |
|---|---|---|---|
| 4,940,900 | A | 7/1990 | Lambert |
| 5,349,189 | A * | 9/1994 | Maggard ............... 250/339.12 |
| 5,452,232 | A | 9/1995 | Espinosa et al. |
| 6,087,662 | A | 7/2000 | Wilt et al. |
| 2005/0040072 | A1 | 2/2005 | Respini et al. |

FOREIGN PATENT DOCUMENTS

| | | | |
|---|---|---|---|
| EP | 304233 A1 * | 2/1989 | |
| WO | WO 2004042375 A1 * | 5/2004 | |

OTHER PUBLICATIONS

"Evaluation of a Novel Method to Study Oil Stability", J.-A. Östlund, T. Russel, S. Walker, Å. HÅkansson, L. Greek, G. Richards.
"Standard Test Method for Determination of Intrinsic Stability of Asphaltene-Containing Residues, Heavy Fuel Oils, and Crude Oils (n-Heptane Phase Separation; Optical Detection)1", ASTM Internationl, Designation D 7157—05, pp. 1-9.
"Test Methods for Determining Asphaltene Stability in Crude Oils", S. Asomaning, Petroleum Science and Technology, vol. 21. Nos. 3 & 4, pp. 581-590, 2003.
"Asphaltene Aggregation from Crude Oils and Model Systems Studied by High-Pressure NIR Spectroscopy", N. Aske, H. Kallevik, E. Eng Johnsen, J. Sjöblom, Energy & Fuels, vol. 16, No. 5, pp. 1287-1295, 2002.
"Solubility Parameters Based on IR and NIR Spectra: I. Correlation to Polar Solutes and Binary Systems", M. Fossen, P. Viggo Hemmingsen, A. Hannisdal, J. Sjoblöm, H. Kallevik, Journal of Dispersion Science and Technology, vol. 26, No. 2, pp. 227-241, Mar. 2005.

* cited by examiner

*Primary Examiner* — David P Porta
*Assistant Examiner* — Casey Bryant
(74) *Attorney, Agent, or Firm* — Edward O. Yonter; Michael B. Martin

(57) ABSTRACT

A method of predicting the stability of a hydrocarbon process stream is disclosed and claimed. The method includes obtaining samples from one or more process streams and measuring the actual stability and the near infrared spectral absorbance of those samples. A classification model is initially developed to identify sample subsets and correlation model is created using the stability and absorbance data by inserting that data into a mathematical function. Online or offline measurements are then taken from the hydrocarbon process stream, the classification model is used initially to identify the subset and corresponding correlation model is used to predict the stability of the stream.

15 Claims, 6 Drawing Sheets

NIR Spectrum of Visbroken Residue

METHOD FOR PREDICTING HYDROCARBON PROCESS STREAM STABILITY USING NEAR INFRARED SPECTRA

TECHNICAL FIELD

This invention relates generally to predicting hydrocarbon process stream stability. More specifically, the invention relates to creating a correlation model to predict hydrocarbon process stream stability using near infrared absorbance. The invention has particular relevance to predicting stability of a hydrocarbon process stream by measuring a near infrared absorbance and comparing the measured absorbance against a correlation model.

BACKGROUND

Crude oil typically contains several hundred thousand compounds. A common simplified analysis system classifies these compounds into four groups according to their solubility. This system is known as "SARA" analysis, where the groups are saturates, aromatics, resins, and asphaltenes. The least soluble of these groups are the asphaltenes, which can be stabilized by association with resins and/or aromatics but are destabilized by association with saturates. Asphaltenes typically exist as nano-scale stabilized dispersion in the resin, aromatics, and saturates mix. If the balance of these components is disturbed, as it can be during thermal cracking, conditions may arise where asphaltenes precipitate from solution. Among other problems, this thermal cracking can lead to coke formation at high temperatures and sludge in visbreaker tar residue.

Asphaltenes are of particular interest to the petroleum industry because of their depositional effect in production equipment. Asphaltenes also impart high viscosity to crude oils, negatively impacting production. Variable asphaltene concentration in crude oils within individual reservoirs creates a myriad of production problems. Refining of heavier crudes poses problems to petroleum producers and refiners. During production, unwanted asphaltene precipitation causes well plugging. During refining, asphaltenes cause refinery heat exchanger fouling, as well as catalyst poisoning by coking or binding of active sites with heavy metals.

Asphaltenes in crude oil, fuel oil, distillation residue, and the like are insoluble in heptane at its boiling point and soluble in benzene at its boiling point. They are typically black to dark brown solids having a molecular structure of polynuclear aromatic rings with alkyl side chains and heteroatoms, such as nitrogen, oxygen, and sulfur. These solubility characteristics allow its indirect measurement.

For example, U.S. Pat. No. 4,940,900 to Lambert discloses measurement of the flocculation threshold of a petroleum product containing asphaltenes by continuously adding a precipitant and measuring the near infrared radiation transmitted through a sample of the product in relation to the quantity of added precipitant. The method requires addition of both a solvent and precipitant to the asphaltene-containing product tested. U.S. Pat. No. 5,452,232 to Espinosa et al. discloses a method of determining properties and yield of a hydrocarbon conversion product from the NIR spectrum of the feedstock. Mid infrared has also been used to determine the functional groups in asphaltenes by methyl ratio, paraffinic and naphthenic carbons, and alkyl side chain length.

Current practice for determining the asphaltene stability of hydrocarbon process streams involves using some form of a heptane phase separation method. In that method, heptane is added to a sample from a hydrocarbon process stream, which dilutes the sample and decreases its absorbance. At the end point, the absorbance begins to increase due to asphaltene (or other condensed aromatic compound) precipitation. Asphaltene stability is than calculated based upon the absorbance readings. A typical method of this type is described in detail in "Standard Test Method for Determination of Intrinsic Stability of Asphaltene-Containing Residues, Heavy Fuel Oils, and Crude Oils (n-Heptane Phase Separation; Optical Detection), published by ASTM International in May 2005 under "Designation D7157-05)." In addition to being time-consuming, a disadvantage of this method is that it requires multiple dilutions of the sample, each then being titrated with the n-heptane solvent for evaluation. These methods also significantly limit the ability to optimize the cracking process, especially under conditions of frequent changes in the type of crude oil in the feedstream.

There thus exists an ongoing need for improved methods of determining stability in hydrocarbon process streams. A particular need exists for quickly and efficiently determining process stream stability with frequent changes in feed type.

SUMMARY

This invention relates to a method of predicting stability in a hydrocarbon process stream using a near infrared spectrum combined with a correlation model. In an aspect, the method includes measuring a stability value corresponding to each of a plurality of samples from the hydrocarbon process stream to produce a first dataset; selecting one or more wave numbers in the near infrared ("NIR") spectrum as a first spectrum; using the first spectrum to determine an absorbance corresponding to each of the plurality of samples to produce a second dataset; incorporating the first dataset and the second dataset into at least one mathematical function to create the correlation model; selecting one or more wave numbers in the NIR spectrum as a second spectrum; using the second spectrum to measure an absorbance corresponding to one or more additional samples; calculating a predicted stability value corresponding to the additional sample(s) by using the measured absorbance as input for the correlation model and receiving as output the predicted stability; and optionally storing the received output in an electronic storage device and/or displaying the received output on a display device.

In another aspect, the method includes categorizing the hydrocarbon process stream into a plurality of different processes; selecting one of the processes; measuring a stability value corresponding to each of a plurality of samples from one of the processes to produce a first dataset; selecting one or more wave numbers in the NIR spectrum as a first spectrum; using the first spectrum to determine an absorbance corresponding to each of the plurality of samples to produce a second dataset; incorporating the first dataset and the second dataset into at least one mathematical function to create the correlation model; selecting one or more wave numbers in the NIR spectrum as a second spectrum; using the second spectrum to measure an absorbance corresponding to one or more additional samples; calculating a predicted stability value corresponding to the additional sample(s) by using the measured absorbance as input for the correlation model and receiving as output the predicted stability; and optionally storing the received output in an electronic storage device and/or displaying the received output on a display device.

It is an advantage of the invention to provide a method of predicting the stability of a hydrocarbon process stream by defining a range of the NIR spectra and incorporating measured absorbance into one or more mathematical functions.

Another advantage of the invention is to provide a method of gathering stability data from a plurality of hydrocarbon process streams and creating a correlation model from that data to allow calculation of a predicted stability based solely upon NIR spectral measurements.

An additional advantage of the invention is to provide a method of analyzing a feed sample to select an optimum correlation model for use in analyzing the corresponding cracked residue sample.

A further advantage of the invention is to provide an improved efficient method for analyzing cracked residue samples that reduces the amount of time required as compared to existing methodologies.

Another advantage of the invention is to provide a user-friendly method of analyzing cracked residue samples that requires less skill and training than current methodologies.

Yet another advantage of the invention is to provide an online method of analyzing cracked residue sample to optimize the cracking process.

Additional features and advantages are described herein, and will be apparent from, the following Detailed Description, Figures, and Examples.

DETAILED DESCRIPTION

The disclosed method may be applied to any number of process or refinery streams in which asphaltene components are stabilized or solubilized and is not limited to any particular type of hydrocarbon process stream. Representative examples include crude oil (spanning the range from high asphaltic or sour to low asphaltic or sweet), atmospheric distillation bottom feeds, residuals, crude unit vacuum bottom feeds, pipelined crude oil, solvent deasphalting bottoms products, and other refinery streams. The method may also be applied to, for example, heavy fuel oil. Application of the disclosed method is envisioned in any type of petroleum product in any phase of the refining process in which asphaltenes are stabilized or solubilized. Depending upon the type of sample used, the number of samples required to produce an accurate predictive correlation model may vary, as explained in more detail below.

In one embodiment, the method relates to predicting stability in a hydrocarbon process stream using NIR spectral absorbance measurements combined with a correlation model. The method includes numerous steps and dataset generation to create the correlation model. In a preferred embodiment, the stability of each of a plurality of samples from the hydrocarbon process stream is measured using any suitable technique. One such technique is n-heptane phase separation as described in ASTM Designation: D7157-05, published as "Standard Test Method for Determination of Intrinsic Stability of Asphaltene-Containing Residues, Heavy Fuel Oils, and Crude Oils (n-Heptane Phase Separation; Optical Detection). This set of measurements produces a first dataset that are used in conjunction with one or more additional datasets to create the correlation model.

Based upon the first dataset, the method includes selecting one or more wave numbers in the NIR spectrum as a first spectrum. For each sample having its stability measured, an absorbance corresponding to each of the plurality of those samples is measured to produce a second dataset. The first dataset and the second dataset are then incorporated into a mathematical function to create the correlation model.

In an embodiment, the method includes classifying the plurality of samples based upon the first dataset and/or the second dataset. The classification is typically done in one of two ways. In one embodiment, for example in thermal cracking processes, along with each sample of the cracked residue (vistar in the case of Visbreakers) a corresponding sample is taken of the feed to the unit, from which the cracked residue is derived. The NIR spectra of the feeds is recorded and analyzed using a statistical classification technique, such as Principal Component Analysis, Neural Network Analysis, etc., to create a third dataset. The classification for the modeling of the first and second dataset is based on this third dataset. In an alternative embodiment, the NIR spectra of the cracked residue samples themselves are used in the initial classification analysis. Separate Partial Least Squares (PLS) models are then derived for the different classification groups identified.

The correlation model may be used to predict a stability value for one or more additional samples by selecting one or more wave numbers in the NIR spectrum as a second spectrum and using the second spectrum to measure an absorbance value for the additional sample(s). The method further includes calculating a predicted stability value corresponding to the additional sample(s) by using the measured absorbance in the second spectrum as input for the correlation model and receiving as output the predicted stability. In an embodiment, the first spectrum and the second spectrum at least partially overlap. In another embodiment, the first spectrum and the second spectrum are identical. It should be appreciated that generally NIR spectra differences are subtle and appear nearly identical to the naked eye. Typically, slight shoulders and broadening of peaks will be observed.

Typically, the main region of the NIR spectrum that holds information predictive of the stability and including the first spectrum and/or the second spectrum have wave numbers from about 7,500 cm$^{-1}$ to about 4,000 cm$^{-1}$. The selection of regions of the NIR spectrum for inclusion in the model is typically accomplished through an iterative process using PLS (or other suitable function) analysis and suitable statistical software known in the art. Models for different classifications for different degrees of robustness may be based on different regions of the spectrum. A model may be based, for example, on one or more regions, such as based on three regions including from about 4,400 cm$^{-1}$ to about 4,200 cm$^{-1}$, from about 5,600 cm$^{-1}$ to about 5,900 cm$^{-1}$, and from about 7,000 cm$^{-1}$ to about 7,500 cm$^{-1}$. Alternatively, a single region such as from about 4,500 cm$^{-1}$ to about 4,000 cm$^{-1}$ may be used. The selected region may also depend on any pre-processing that has been carried out on the basic spectral absorbance data, which may include baseline correction, calculation of first or second order derivatives, or other suitable techniques.

Though a variety of highly condensed aromatic compounds may be detected in determining or predicting the stability of a particular sample, asphaltenes and/or asphaltene-containing residues typically are the detected species. In creating the first dataset that will comprise part of the information used to create the correlation model using the mathematical function, the plurality of samples measured may, in alternative embodiments, be either from a same hydrocarbon process stream or a different hydrocarbon process stream. For example, a subset of the plurality of samples may obtained from a particular type of hydrocarbon process stream (e.g., bottom fraction, blended fuel oil, gas oil, etc.) at a particular location and another subset may be obtained from the same type of hydrocarbon process stream at another location. The measured stability values of the samples from the two locations may be combined to form one dataset.

It is contemplated that such datasets may be formed from samples obtained from one, two, or more hydrocarbon process streams of the same type, at either the same location or different locations. Process streams at different locations and of a different type may also be used. In the latter case, the different types of process streams typically need to be compatible from an NIR spectra standpoint. Typically, this method is applicable to hydrocarbon process streams where the solution stability of the asphaltene (or other highly condensed aromatic species) is dependent on the solvency power of the solvent or dispersing component of the hydrocarbon. The solution stability is also dependent generally on the balance of saturate and aromatic components that make up the solvent or dispersing component.

In an embodiment, the samples (including the samples for creating the first dataset, second dataset, other datasets, and the samples to be predicted) are derived from an uncracked hydrocarbon process stream. In another embodiment, such samples are derived from a cracked hydrocarbon process stream. Sample sets could be derived from a multitude of sources including, for example, crude oils; crude oil atmospheric distillation residues; crude oil vacuum distillation residues; blended heavy fuel oils; or residues from thermal cracking process that contain asphaltenes, cracked asphaltenes, or polycyclic species that have been generated during the cracking process.

Other potential characterizations of a hydrocarbon feed may include atmospheric residue or heavy vacuum residue in terms of its potential to foul, or a basic "Stability" index. Characteristics could be related to crude preheat fouling, vacuum furnace fouling, visbreaker furnace fouling, coker furnace fouling, or the like.

Many of these characteristics are reflected to some degree in the NIR spectra, allowing the SARA analysis for crude oils to be predicted from those spectra using a mathematical correlation. Such predicted characteristics result from a complex balance of a vast range of components. For example, in developing a correlation between the NIR spectra and stability, a range of "vistars" was gathered and stability was determined by a standard method and the NIR spectra were recorded under specific conditions. In this example, a partial least squares analysis was used to develop a correlation between certain regions of the NIR spectrum and stability. A number of models may be generated with different degrees of predictability depending on factors, such as the specific regions of the spectra used and the type of pre-processing performed with the spectra (i.e., using background correction, taking derivatives, other mathematical functions and transformations, etc.). Some of these models have very similar degrees of predictability.

Figure 1:
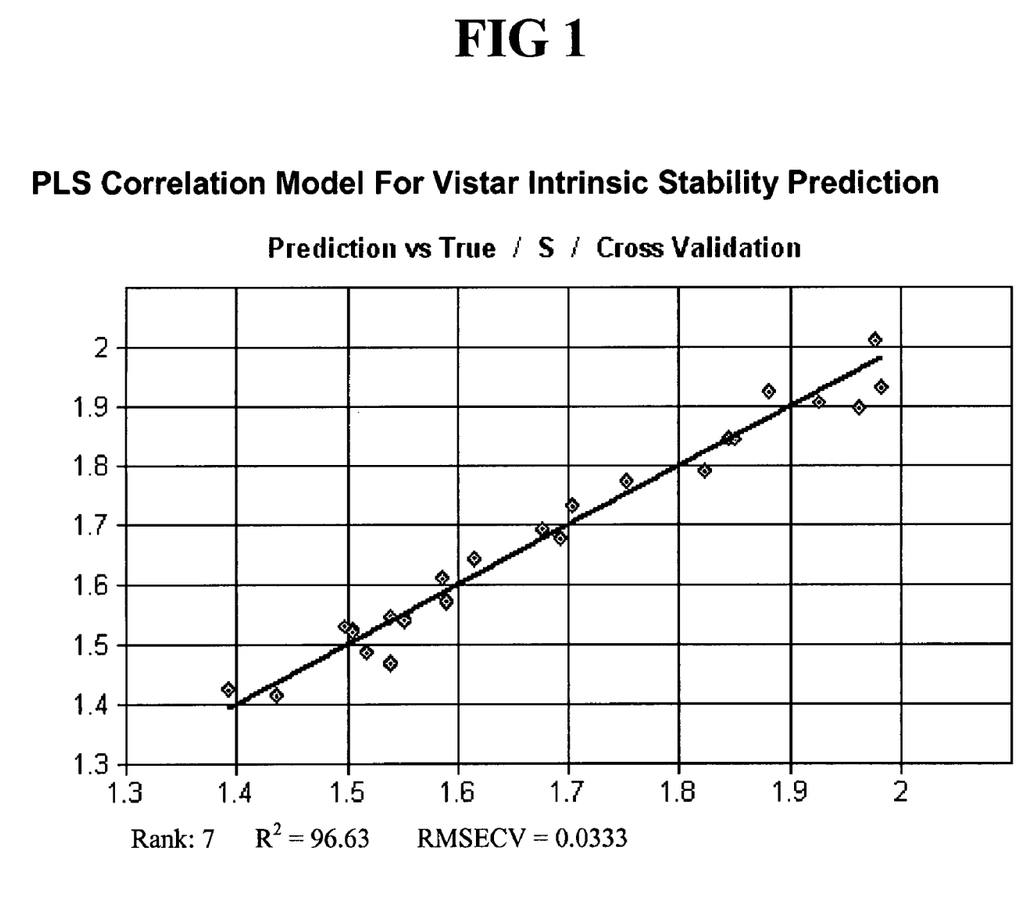
FIG. 1 illustrates the accuracy of predicted stability values using a representative correlation model.

Generally, a correlation model that includes datasets from a broad range of different process streams produces a more robust model. The broader the "class" of materials incorporated in a correlation model, the more robust and powerful the resulting correlation model. In certain cases, such a robust model may have increased confidence intervals for the predicted result. Conversely, a narrower class of materials typically produces a more accurate correlation, but the model is then limited to a narrower range of materials or process streams. Defining such "classes" of materials would be apparent to those skilled in the art. A representative strategy includes using the NIR spectra of uncracked samples to classify the corresponding cracked samples to be tested and to use those groups of samples to build different correlation models. A wide range of uncracked feeds is typically required on the actual cracking unit to define such classifications, whereas in other cases, such as blended fuel oil, gas oil, etc., fewer samples may be sufficient to produce an adequate model. FIG. 1 illustrates the accuracy of predicted stability values using a representative PLS correlation model (rank indicates the number of principle components in the particular correlation model used).

According to an embodiment, such a classification scheme would generally require running two spectra initially, one for the feed to determine which regression model to use, and a second for one or more of the cracked samples to calculate the stability or "S" value. The cracked sample spectra would be processed in two steps, initially by classification analysis (e.g., principle component analysis), followed by analysis for the stability or "S" value using a suitable correlation model. Alternatively, NIR spectra of the cracked residue samples could be used in the initial classification analysis. Separate models (e.g., PLS) may then be derived for the different classification groups identified. In this case, the NIR spectral analysis occurs in two stages. The first stage includes a principal component classification model to determine class and the associated correlation model. The second includes applying the appropriate analysis technique (e.g., PLS) to predict stability.

It should be appreciated that any mathematical technique and/or statistical technique that may logically incorporate the first and second datasets to produce the correlation model may be used. In an embodiment, the mathematical function includes a statistical treatment method. In another embodiment, the mathematical function includes any suitable manual or computer algorithm-based protocol to produce the correlation model. Representative types of mathematical functions including but are not limited to linear regression, nonlinear regression, and neural network analysis. It should be appreciated that any general correlation method would be applicable for this described method. In an embodiment, the particular model or function used to create the correlation model may be changed or adjusted depending upon the generated and acquired datasets.

In alternative embodiments, the NIR absorbance may be read on-line (continuous or intermittent) and using the described classification/correlation strategy the determination of stability or "S" value could be automatic. Such online measurements may be analyzed in real-time or with a user-defined or other delay. For example, online measurements may take place by using a side-stream, inline, or other suitable flow-through device.

A manual operator or an electronic device having components such as a processor, memory device, digital storage medium, cathode ray tube, liquid crystal display, plasma display, touch screen, or other monitor, and/or other components may be used to execute all or parts of the described method. In certain instances, the controller may be operable for integration with one or more application-specific integrated circuits, programs, computer-executable instructions, or algorithms, one or more hard-wired devices, wireless devices, and/or one or more mechanical devices. Some or all of the controller system functions may be at a central location, such as a network server, for communication over a local area network, wide area network, wireless network, Internet connection, microwave link, infrared link, and the like. In addition, other components such as a signal conditioner or system monitor may be included to facilitate signal-processing algorithms. It is also contemplated that any needed sensors, couplers, connectors, or other data measuring/transmitting equipment may be used to capture and transmit data.

The foregoing may be better understood by reference to the following examples, which are intended only for illustrative purposes and are not intended to limit the scope of the invention.

EXAMPLE 1

For a series of 24 vistar samples, the "Stability" and NIR spectra were determined using accepted standard methodology. Using a partial least squares statistical methodology, a correlation model was developed between the standard stability measurement and the absorbance measurement in selected regions of the NIR spectrum. The model was validated using a cross validation technique, where one sample at a time was left out of the correlation model and predicted from that correlation.

For purposes of this Example, the stability of a series of vistar samples was determined in accordance with method ASTM Designation: D7157-05, published as "Standard Test Method for Determination of Intrinsic Stability of Asphaltene-Containing Residues, Heavy Fuel Oils, and Crude Oils (n-Heptane Phase Separation; Optical Detection). This method assumes a model of the oil covering the general concept of asphaltene stability in an oil matrix. For example, the oil may be modeled as consisting of asphaltenes existing as a stable colloidal dispersion in an oil matrix.

Figure 2:
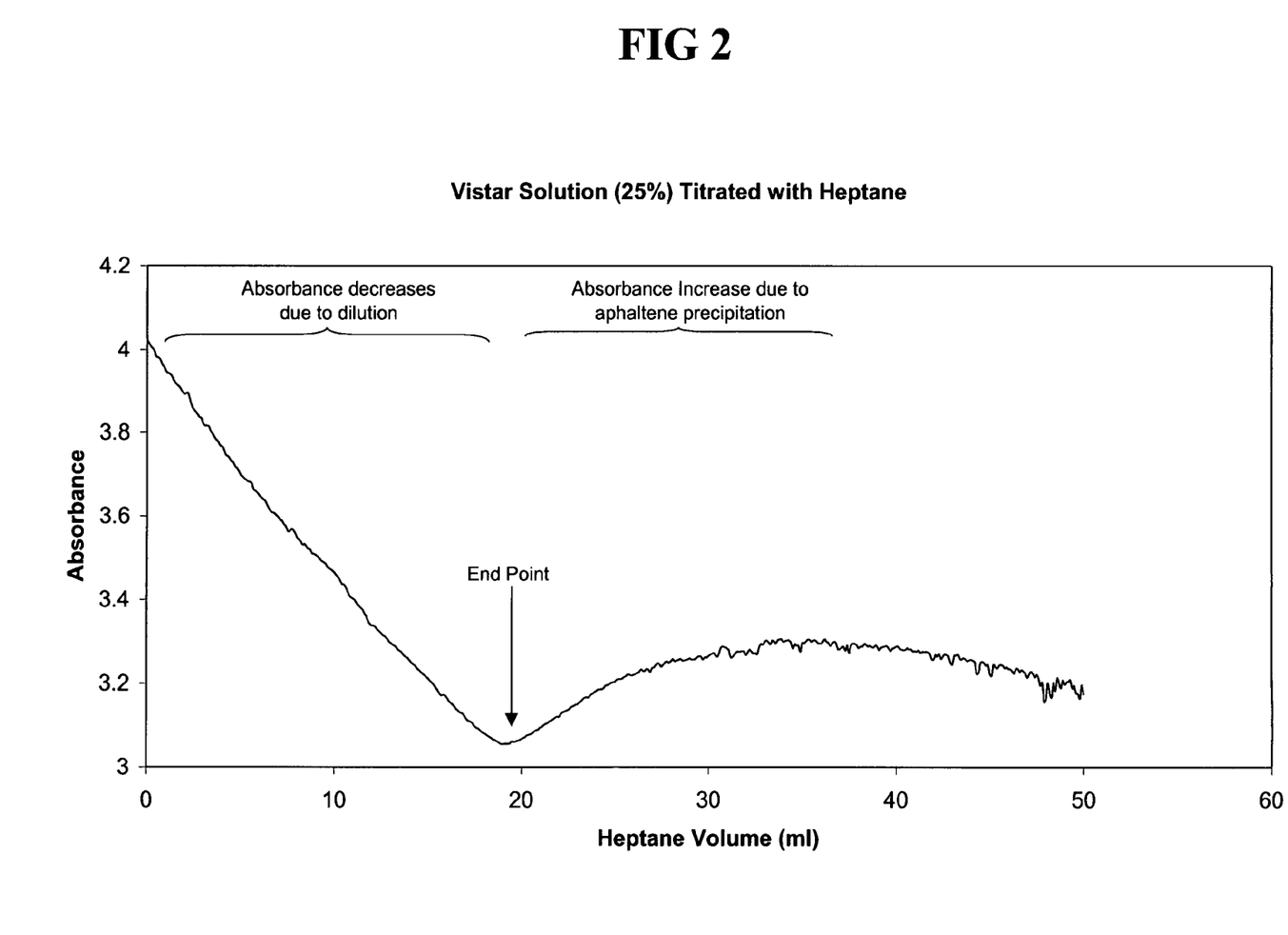
FIG. 2 shows an exemplary absorbance plot of a 25% vistar concentration titrated with n-heptane. At a point, the solubility balance in the solution causes dissolved asphaltenes to precipitate as black particulates. This precipitation creates a sudden increase in the absorbance and is the titration end point.

Three dilutions were prepared for each vistar sample using toluene as a diluent of approximately 25%, 50%, and 70% concentration. In turn, the diluted samples were fitted into an apparatus fitted with a stirrer and an optical probe for measuring the absorbance of the solution. The solution was titrated with heptane and the absorbance measured as a function of added heptane, as described in ASTM Designation: D7157-05. Titration with n-heptane initially causes a reduction in absorbance as a function of dilution. At some point, the solubility balance in the solution causes dissolved asphaltenes to precipitate as black particulates. This precipitation creates a sudden increase in the absorbance and is the titration end point. The ratio of toluene to heptane in the solution at this end point is termed the "Flocculation Ratio" ("FR"). FIG. 2 illustrates a typical absorbance plot for such a titration with a 25% vistar concentration. FR was determined for each vistar concentration.

Figure 3:
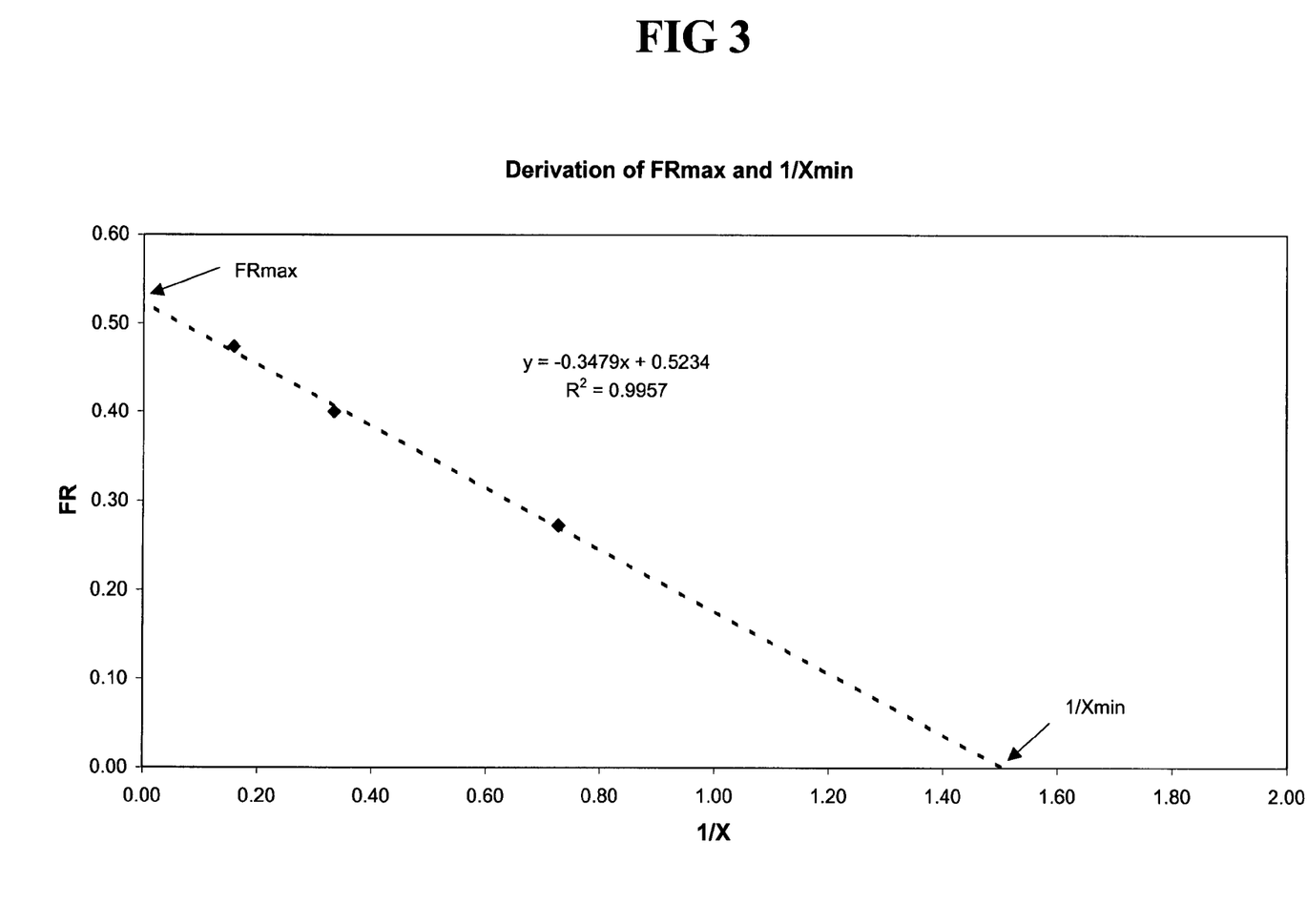
FIG. 3 represents derivation of FRmax and 1/Xmin, where FRmax is the flocculation ratio when 1/X=0 and 1/Xmin is a measure of the heptane volume needed for flocculation in the undiluted oil.

FR was plotted against the ratio of vistar to solvent (i.e., toluene+heptane) that existed at the end point, termed 1/X. A least squares linear regression line for the three points was then plotted (shown in FIG. 3). Two points were determined by extrapolation from this plot: (i) FRmax: the flocculation ratio when 1/X=0 and (ii) 1/Xmin: which is a measure of the heptane volume needed for flocculation in the undiluted oil. This data was used to calculate the following three oil stability parameters: (i) Sa: peptisability of asphaltenes in the vistar (i.e., a measure of the inherent solubility of the asphaltenes); (ii) So: peptising power of the oil matrix (i.e., ability of the oil matrix to stabilize/solubilize asphaltenes); and (iii) S: intrinsic stability of the oil (i.e., measure of the stability of asphaltenes in this particular oil system). Where, Sa=1−FRmax; So=(FRmax)×(1+Xmin); and S=1+Xmin.

Figure 4:
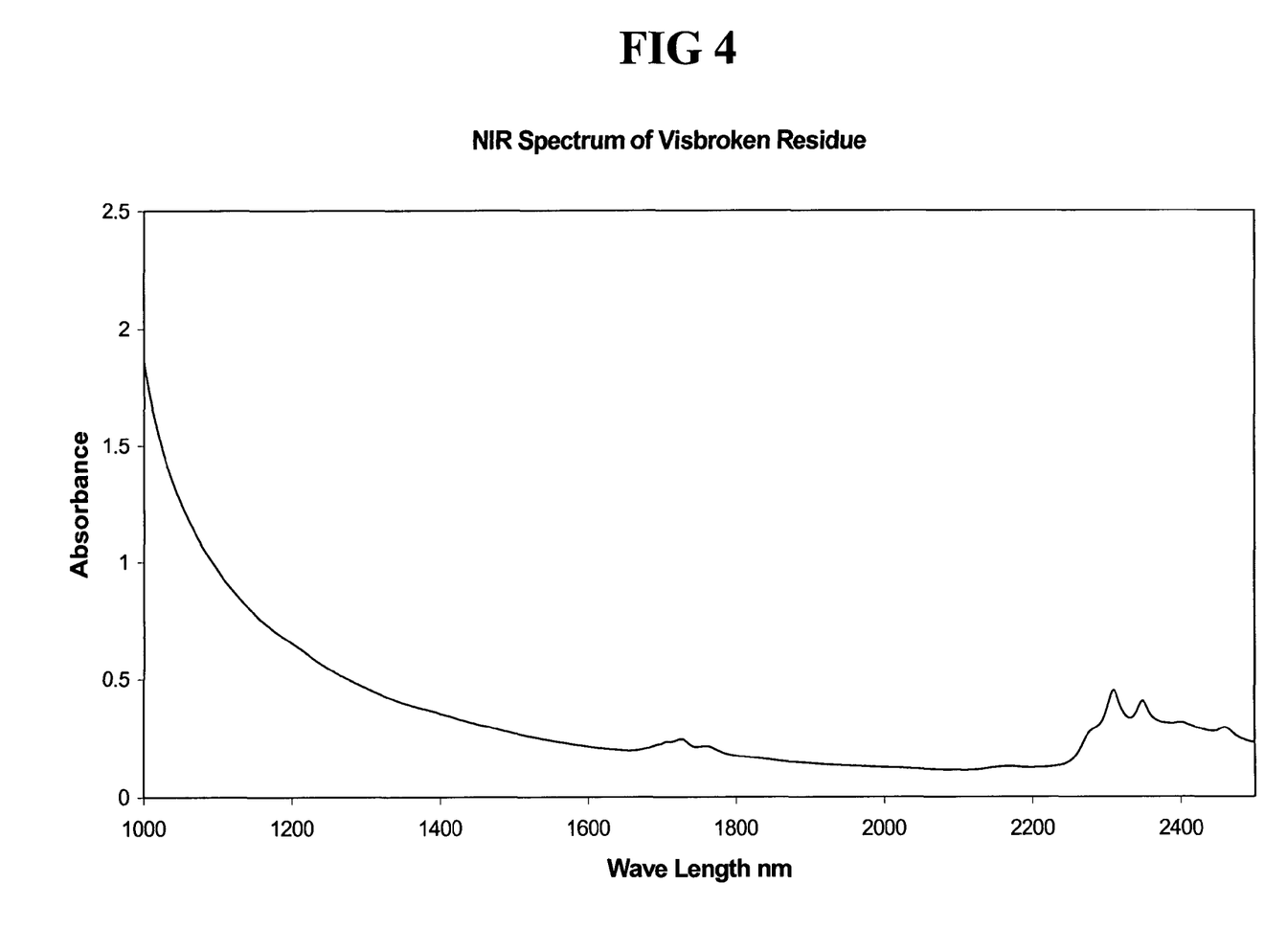
FIG. 4 depicts a typical NIR spectral absorbance plot for visbroken residue.

The NIR spectra of the samples were determined using a Bruker MPA FTNIR instrument. The measurements were made in transmission mode using a 0.2 mm path-length cell. The spectra were recorded at a sample temperature of 60° C. An example of a typical NIR spectrum of vistar is shown in FIG. 4.

EXAMPLE 2

This Example is a model for predicting stability based on a partial least squares analysis of 24 "vistar" samples using the technique described in Example 1. This model covers regions of the NIR spectrum including 6102 to 5446 $cm^{-1}$ and 4601 to 4247 $cm^{-1}$ and uses 7 principle components. The components are statistical orthogonal variables derived from the PLS analysis. The statistical parameters for the model were $R^2$=0.948 and RMSEV=0.0423. Representative results are shown for three of the samples in Table 1.

TABLE 1

| Actual "S" Stability | Predicted "S" Stability |
|---|---|
| 1.70 | 1.64 |
| 1.45 | 1.53 |
| 1.98 | 2.05 |

EXAMPLE 3

In principle, the described system could be adapted for online monitoring. A side stream from the cracked vistar bottoms product could be fed to a monitoring unit where the NIR spectrum could be measured. A computer system would be operable to compare the spectrum of the vistar with the correlation model and calculate the predicted stability result. This result could be transmitted to a control system and acted on manually or integrated into a control scheme whereby, based on the result, the thermal cracking process severity would be increased or decreased. The specific calibration model for this mode of operation could be automatically determined with a similar online system monitoring the feed to the unit. Alternatively, because the feed need only be tested each time it changes, the required increase or decrease in thermal cracking severity could also be determined by taking grab samples of the feed for analysis and manually selecting the correlation model for the vistar analysis.

EXAMPLE 4

Initial development of calibration model(s) for implementing the method of the invention may include collecting both feed and vistar (cracked bottoms) samples on a regular basis. The sampling period, for example several weeks, would cover operating conditions including the range of conditions that the unit could potentially experience under normal operation. In this Example, the collected samples (both feed and vistar) were analyzed using a commercially available FTIR NIR spectrometer. The spectra were run in transmission mode using 0.5 mm pathlength cells. The vistar samples were also analyzed for asphaltene stability using the method ASTM D7157-05 (as explained above). This test resulted in "S" stability values for each vistar sample.

Figure 5:
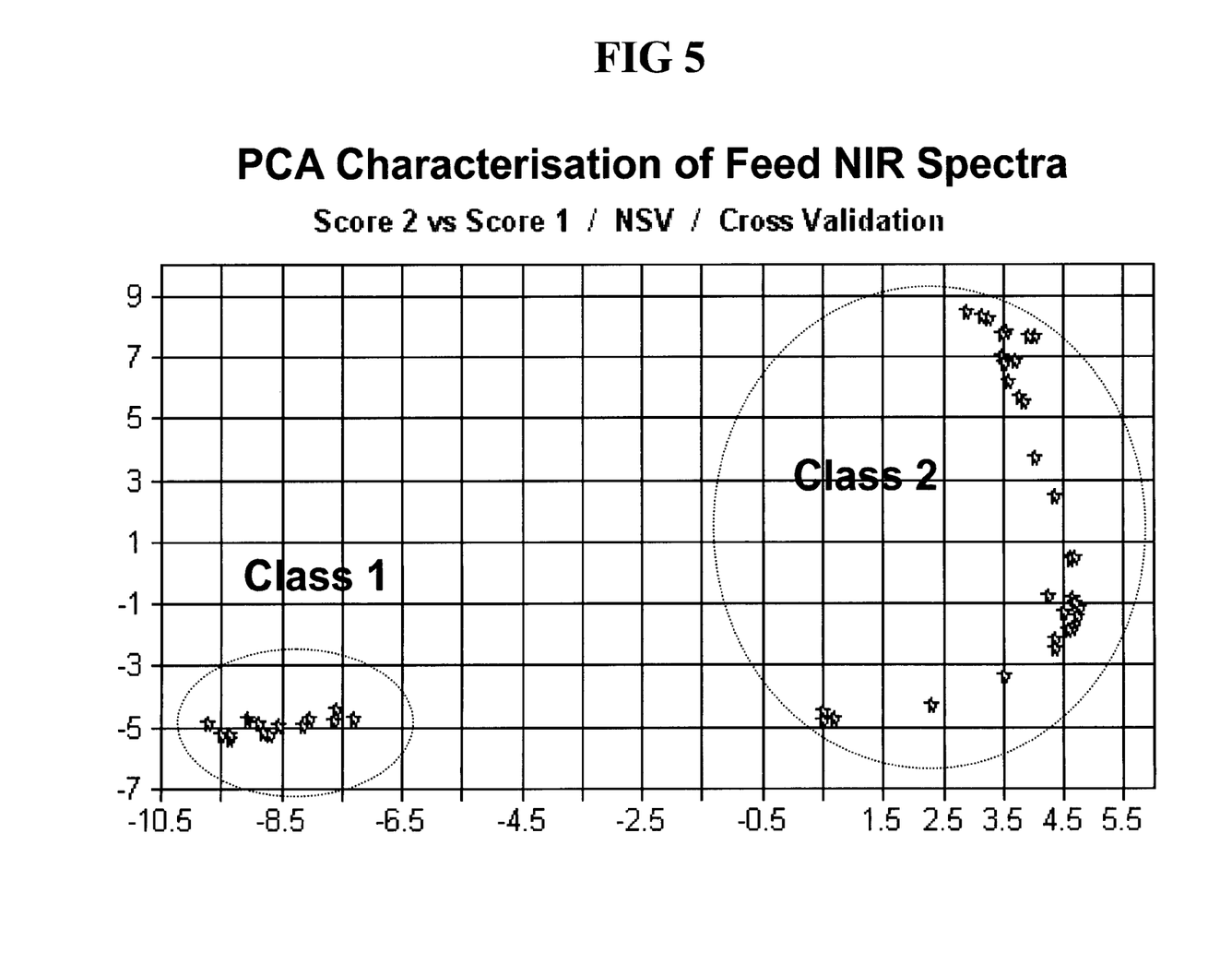
FIG. 5 shows an exemplary PCA characterization of feed NIR spectra, as explained in Example 4.
Figure 6:
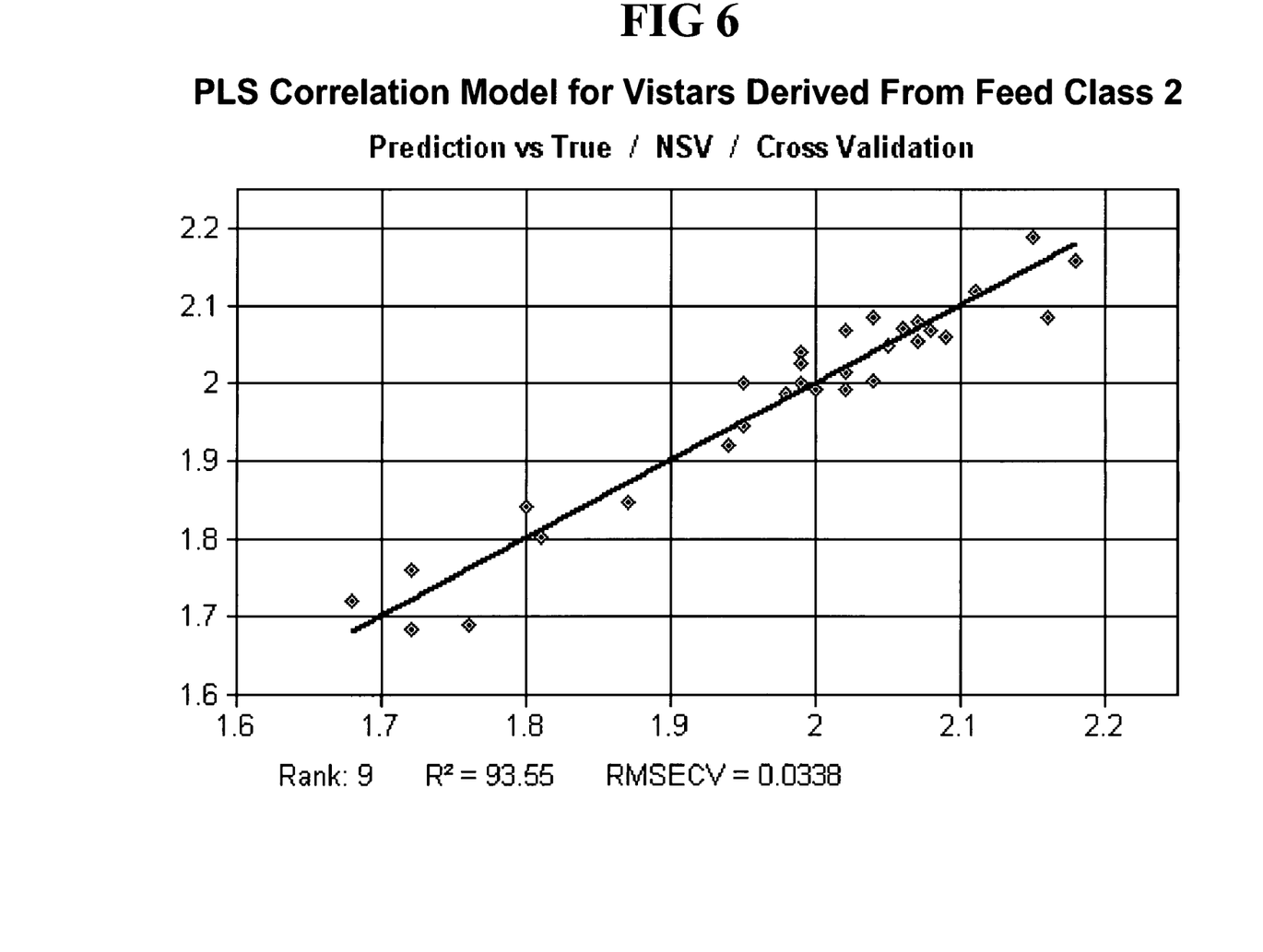
FIG. 6 illustrates an example of the stability predicted by the method of the invention as compared to the experimentally determined stability, as explained in Example 4.

The feed spectra were analyzed using the statistical technique of principal component analysis (PCA). A typical scores plot for the sample set is shown in FIG. 5. It was observed that feeds run over the test period were of two types, shown as "Class 1" and "Class 2" in FIG. 5. The vistar sample spectra were then separated into two groups corresponding to the feed class from which they were derived. Partial Least Squares (PLS) analysis was then carried out to develop correlations between the vistar spectra absorbance and the previously determined ASTM D7157 intrinsic stability (i.e., "S" values). Separate correlation models were developed for the two groups of vistars derived from the corresponding groups of feeds as classified by principal component analysis. An exemplary correlation between the stability predicted by the method of the invention and the experimentally determined stability (from feed "Class 2") is shown in FIG. 6 (rank indicates the number of principle components used in the particular correlation model).

In operation, the feed and vistar samples would be collected on a regular basis (batch, online, sidestream, etc. as explained above) and the NIR spectra collected. The feed spectra would be analyzed using a, for example PCA classification model, to determine the corresponding feed class, which in turn is used to determine the proper correlation model to predict the stability from the vistar spectrum. The predicted stability is then used to adjust variables controlling the severity of the visbreaker to optimize its cracking operation.

It should be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

The claimed invention is:

1. A method of predicting stability in a hydrocarbon process stream using a near infrared spectrum combined with a correlation model, the method comprising:
   (a) measuring a stability value corresponding to each of a plurality of samples from the hydrocarbon process stream to produce a first dataset;
   (b) selecting one or more wave numbers in the near infrared spectrum as a first spectrum;
   (c) using the first spectrum to determine an absorbance corresponding to each of the plurality of samples from step (a) to produce a second dataset;
   (d) incorporating the first dataset and the second dataset into at least one mathematical function to create the correlation model;
   (e) selecting one or more wave numbers in the near infrared spectrum as a second spectrum;
   (f) using the second spectrum to measure an absorbance corresponding to one or more additional samples;
   (g) calculating a predicted stability value corresponding to the additional sample(s) by using the measured absorbance from step (f) as input for the correlation model and receiving as output the predicted stability; and
   (h) optionally storing the received output in an electronic storage device and/or displaying the received output on a display device.

2. The method of claim 1, including classifying the plurality of samples based upon the first dataset and/or the second dataset.

3. The method of claim 1, wherein the first spectrum and the second spectrum at least partially overlap.

4. The method of claim 1, wherein the first spectrum and the second spectrum are identical.

5. The method of claim 1, wherein the first spectrum and/or the second spectrum have wave numbers from about 7,500 $cm^{-1}$ to about 4,000 $cm^{-1}$.

6. The method of claim 1, wherein the stability and the predicted stability are based upon asphaltenes and/or asphaltene-containing residues in the hydrocarbon process stream.

7. The method of claim 1, wherein each of the plurality of samples in step (a) is from a same hydrocarbon process stream.

8. The method of claim 1, wherein one or more of the plurality of samples in step (a) is from a different hydrocarbon process stream, each said stream being a same type.

9. The method of claim 1, wherein one or more of the plurality of samples in step (a) are derived from a process stream selected from the group consisting of: an uncracked hydrocarbon process stream and a cracked hydrocarbon process stream.

10. The method of claim 1, including measuring a plurality of samples from a plurality of different hydrocarbon process streams to compile the first dataset and the second dataset.

11. The method of claim 1, wherein the correlation model is selected from the group consisting of: linear regression analysis; nonlinear regression analysis; and neural network analysis.

12. The method of claim 1, including operating the method over a network.

13. The method of claim 12, wherein the network is an Internet.

14. A digital storage medium having computer-executable instructions stored thereon, the instructions operable to execute the method of claim 1.

15. A method of predicting stability in a hydrocarbon process stream using a near infrared spectrum combined with a correlation model, the method comprising:
   (a) categorizing the hydrocarbon process stream into a plurality of different processes;
   (b) selecting one of the processes;
   (c) measuring a stability value corresponding to each of a plurality of samples from one of the processes to produce a first dataset;
   (d) selecting one or more wave numbers in the near infrared spectrum as a first spectrum;
   (e) using the first spectrum to determine an absorbance corresponding to each of the plurality of samples from step (a) to produce a second dataset;
   (f) incorporating the first dataset and the second dataset into at least one mathematical function to create the correlation model;
   (g) selecting one or more wave numbers in the near infrared spectrum as a second spectrum;
   (h) using the second spectrum to measure an absorbance corresponding to one or more additional samples;
   (i) calculating a predicted stability value corresponding to the additional sample(s) by using the measured absorbance from step (f) as input for the correlation model and receiving as output the predicted intrinsic stability; and
   (j) optionally storing the received output in an electronic storage device and/or displaying the received output on a display device.

* * * * *